US012575718B2

(12) United States Patent
Yu et al.

(10) Patent No.: US 12,575,718 B2
(45) Date of Patent: Mar. 17, 2026

(54) UNIVERSAL ENDOSCOPE ADAPTER

(71) Applicant: Cornell University, Ithaca, NY (US)

(72) Inventors: Michelle Yu, Ithaca, NY (US); Anais Rameau, Ithaca, IN (US); Mark Lee, Ithaca, NY (US); Elliot Morse, Ithaca, NY (US)

(73) Assignee: Cornell University, Ithaca, NY (US)

( * ) Notice: Subject to any disclaimer, the term of this patent is extended or adjusted under 35 U.S.C. 154(b) by 372 days.

(21) Appl. No.: 18/244,851

(22) Filed: Sep. 11, 2023

(65) Prior Publication Data

US 2024/0081624 A1    Mar. 14, 2024

Related U.S. Application Data

(60) Provisional application No. 63/405,855, filed on Sep. 12, 2022.

(51) Int. Cl.
A61B 1/00          (2006.01)

(52) U.S. Cl.
CPC ........ A61B 1/0014 (2013.01); A61B 1/00121 (2013.01); A61B 1/00188 (2013.01)

(58) Field of Classification Search
CPC .............. A61B 1/0014; A61B 1/00121–00128
See application file for complete search history.

(56) References Cited

U.S. PATENT DOCUMENTS

| | | | | |
|---|---|---|---|---|
| 8,858,425 B2 * | 10/2014 | Farr | A61B 90/37 | |
| | | | 600/110 | |
| 10,029,079 B2 * | 7/2018 | Alexander | A61B 1/00016 | |
| 10,092,243 B2 | 10/2018 | Mirza et al. | | |
| 2007/0265498 A1 * | 11/2007 | Ito | A61B 1/00124 | |
| | | | 348/75 | |
| 2009/0247833 A1 | 10/2009 | Tanaka | | |
| 2013/0102359 A1 * | 4/2013 | Ho | H04M 1/21 | |
| | | | 455/556.1 | |
| 2014/0051923 A1 * | 2/2014 | Mirza | A61B 1/00009 | |
| | | | 600/103 | |
| 2017/0273539 A1 * | 9/2017 | Law | A61B 1/00126 | |
| 2018/0284580 A1 * | 10/2018 | Matthews | A61B 1/00042 | |
| 2019/0000309 A1 * | 1/2019 | Yamamoto | A61B 1/05 | |
| 2022/0192468 A1 * | 6/2022 | Holland | A61B 1/0014 | |

FOREIGN PATENT DOCUMENTS

GB          2495561 A          4/2013

OTHER PUBLICATIONS

Lee, Mark, Assembling Endoscope Phone Adaptor without a Magnifying Lens, May 14, 2022, https://youtu.be/fbqr6GI1IdA.
Lee, Mark, Use Instructions for Endoscope Phone Adaptor without a Magnifying Lens, May 28, 2022, https://youtu.be/fbqr6GI1IdA.
Lee, Mark, Assembling Endoscope Phone Adaptor with Magnifying Lens, May 14, 2022, https://youtu.be/0wqF17mPoNM.
Lee, Mark, Use Instructions for Endoscope Phone Adaptor with a Magnifying Lens, May 14, 2022, https://youtu.be/ywBH8mbj6dE.

* cited by examiner

*Primary Examiner* — Frank Johnson
(74) *Attorney, Agent, or Firm* — Barnes & Thornburg

(57) ABSTRACT

An endoscopy system according to the present disclosure includes an adapter for coupling a mobile device to an endoscope. A guide can be included that enables proper alignment of the adapter with the mobile device so that a generally centered image is presented on the mobile device from the endoscope. Further, various embodiments of the adapter can include integrated optical lenses.

20 Claims, 7 Drawing Sheets

UNIVERSAL ENDOSCOPE ADAPTER

PRIORITY CLAIM

This application claims priority under 35 U.S.C. § 119(e) to U.S. Provisional Application Ser. No. 63/405,855, filed Sep. 12, 2022, which is expressly incorporated by reference herein.

BACKGROUND

Endoscopes are integral tools used in medicine to diagnose and treat disease. It allows for visualization of structures in confined anatomic areas in a minimally invasive manner. Visualization via endoscopy allows the user to identify medical abnormalities, and potentially treat conditions with surgical tools under endoscopic visualization. Endoscopes are used in many settings in medicine, including in the clinic, hospital and operating room. Endoscopes generally come in two forms, with a flexible fiberoptic cord or a rigid telescope with lenses and/or mirrors. There are also several variations depending on the anatomic structure that requires visualization, for example, nasal endoscopes for the nasal cavity and sinuses, flexible laryngoscopes for the pharynx and larynx, bronchoscopes for the trachea and bronchi, laparoscopes for the abdomen, and cystoscopes for the bladder, to name a few.

Base model endoscopes include an eyepiece for viewing images carried by fiber optic cord or telescope. Some complex endoscopes come with a light source, camera cord, and computer processor made by the manufacturer. These components are often stored together in a mobile tower. There can be limitations to this set-up. First, these towers are often large and difficult to transport. They are most commonly stored and used in settings where patients are ambulatory, such as the clinic and operating room. In the inpatient setting, patients' movement may be restricted due to immobility or medical instability, and equipment in these settings often have to be brought to patients' bedsides. Particularly in case of emergencies, devices need to be promptly deployed. In addition, certain geographic settings with limited resources may not be able to afford these devices altogether.

Mobile devices are ubiquitous and have built in high-resolution cameras and/or advanced processing capabilities. Prior technologies have used the cameras/processing capabilities of smartphones to record endoscopic images. Generally, these devices feature a phone case made to fit a specific phone model and a port to attach to and align the lens piece of the endoscope with the phone's camera. These devices may include a telescope for optical magnification, or rely on digital magnification by the phone's software. There can be several limitations to these devices however. First, these devices utilize cases that are designed for specific phone models. Devices cannot be used for alternate models without reconfiguration. Given that phone manufacturers release updated phone models each year and there is a high cost to machining new adaptors and a limited number of people who use endoscopic adaptors, there is a need for a device that can be universally applied to any phone model. Furthermore, these devices primarily target smartphones and no other types of mobile devices, such as tablets and laptops. While phones have the advantage of small size and portability, they are limited by a small screen size that limits ability to visualize procedures under endoscopy. The larger screens for tablets and laptops improves visualization for endoscopists while maintaining portability.

SUMMARY

Devices in line with the present disclosure provide a light that can strobe at a target frequency that is determined by a patient's vocal frequency, detected by a microphone. The device is smaller than the current standard and can fit into the palm of your hand. It attaches to an endoscope/fiberoptic laryngoscope.

According to one aspect of the present disclosure, an adapter kit for coupling a mobile device to an endoscope is described. The kit couples the mobile device to the endoscope so that a camera lens of the mobile device captures an analog image from the endoscope in order that the analog image is displayed as a digital image on an electronic screen of the mobile device.

The kit illustratively includes a mount pad, a scope receiver, and a guide. The a mount pad is provided by a planar plate adapted to be fixed relative to the mobile device by an adhesive layer when the adapter kit is in place relative to the mobile device so that a generally centered digital image is displayed on the mobile device. The scope receiver is coupled to the mount pad. The scope receiver shaped to define a pocket sized to receive an eyepiece included in the endoscope and a camera port opening into the pocket through which the camera lens of the mobile device can receive input. The guide is configured to support alignment of the mount pad and scope receiver relative to the mobile device. In this way, the camera port of the scope receiver is located in alignment with the camera lens of the mobile device to ensure the generally centered digital image is displayed on the mobile device.

In illustrative embodiments, the guide is removably coupled to the scope receiver and shaped to include an alignment aperture smaller than the camera port. The alignment aperture is arranged so that light passing through the alignment aperture forms an alignment indicator shape displayed on the mobile device. The alignment indicator can be moved by movement of the mount pad relative to the mobile device to a selected location on the electronic screen. The selected location is associated with the generally centered digital image prior to the mount pad and scope receiver being fixed in place relative to the mobile device. The alignment aperture can be arranged along an axis around which the camera port extends.

In illustrative embodiments, the kit includes a device case shaped to receive the mobile device. The device case has a back panel formed to include a camera cutout and the mount pad is smaller than the back panel. The back panel is planar so as to provide a flat surface onto which the mount pad is to be fixed by the adhesive layer.

In illustrative embodiments, the guide includes a face plate that extends over one side of the pocket defined by the scope receiver and that is formed to include the alignment aperture. The guide can also includes a cap wall that extends from the face plate to engage a complementary surface of the scope receiver when the guide is coupled to the scope receiver.

In illustrative embodiments, the kit can include a scope retainer. The scope retainer is movable relative to the scope receiver from a locked position in which the eyepiece is blocked from movement out of the pocket of the scope receiver to an unlocked position in which the eyepiece is allowed to move out of the pocket of the scope receiver.

In illustrative embodiments, the guide includes a foot wall. The foot wall can extend from the face plate to engage a complementary surface of the scope retainer when the scope retainer is in the locked position and when the guide is coupled to the scope receiver.

In illustrative embodiments, the alignment aperture has a + shape. Accordingly, light passing through the alignment aperture forms an alignment indicator with the same shape being displayed on the electronic screen of the mobile device.

According to another aspect of the present disclosure, an endoscopy system is described. The system can include an endoscope, a mobile device, a device case, and/or an adapter configured to couple the mobile device and device case to the endoscope.

In illustrative embodiments, the endoscope includes an eyepiece and an optic. The eyepiece can have a view lens and an eye rest flange. The optic can be adapted to carry an analog image to the view lens from a location spaced apart from the eyepiece.

In illustrative embodiments, the mobile device has a camera with a camera lens and an electronic screen coupled to the camera. The electronic screen is configured to display a digital image based on input from the camera lens. The device case receives the mobile device and has a camera cutout through which the camera lens of the mobile device receives input.

In illustrative embodiments, the adapter selectively couples the mobile device and device case to the endoscope so that the camera lens of the mobile device captures the analog image carried to the view lens of the endoscope. In this way, the analog image is displayed as the digital image on the electronic screen for viewing. The adapter illustratively includes a mount pad, a scope receiver, and a scope retainer. The mount pad is fixed to the device case by an adhesive layer. The scope receiver is coupled to the mount pad and has a pocket that receives the eye rest flange of the eyepiece. The scope retainer is movable relative to the scope receiver from a locked position in which the eye rest flange is blocked from movement out of the pocket of the scope receiver to an unlocked position in which the eye rest flange is allowed to move out of the pocket of the scope receive.

In illustrative embodiments, the scope receiver includes a camera-side panel through which the camera port is formed, a receiver body panel that extends away from the camera-side panel, and a scope-side panel that extends from the receiver body panel at a location spaced from the camera-side panel. Using this exemplary configuration, a flange-receiver channel is formed into which the eye rest flange extends is formed by the scope receiver.

In illustrative embodiments, the scope receiver further includes at least one lens arranged along an axis of the camera port between the camera side panel and the scope side panel. The at least one lens may be mounted for movement relative to the scope receiver so as to allow for adjustment of at least one of brightness, focus, focal length, and magnification.

In illustrative embodiments, the scope-side panel forms a U-shape when viewed along an axis of the camera port. Because of this, the flange-receiver channel has open ends at the gap in the U-shape through which the eye rest flange can pass in a direction perpendicular to an axis about which the camera port is formed to enter the flange-receiver channel and pocket of the scope receiver when the scope retainer is in the unlocked position. The scope retainer can include a plug that extends into the open ends of the flange-receiver channel and the pocket of the scope when the scope retainer is in the locked position to block movement of the eye rest flange out of the scope receiver when the scope retainer is in the locked position. The scope retainer includes a flexible lock rib that engages the scope retainer when the scope retainer is in the locked position to resist movement of the scope retainer to the unlocked position.

In illustrative embodiments, the scope retainer is coupled to the mount pad by a releasable clasp. The releasable clasp is provided by a side release male buckle and corresponding catches configured to be engaged by the side release buckle to hold the scope retainer in place relative to the mount pad.

In some embodiments, the system includes a guide. The guide is configured to support alignment of the mount pad and scope receiver relative to the mobile device so that the camera port of the scope receiver is located in alignment with the camera lens of the mobile device to ensure the generally centered digital image is displayed on the mobile device. The guide can be removably coupled to the scope receiver and can be shaped to include an alignment aperture smaller than the camera port. The alignment aperture can be arranged so that light passing through the alignment aperture forms an alignment indicator shape displayed on the mobile device.

In illustrative embodiments, the mobile device can be selected from one of a cell phone, a tablet computer, and a web camera.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 is a perspective view of a endoscopy system in accordance with the present disclosure showing that the system includes an endoscope configured to provide an analog image from a remote location to a user, a mobile device having a camera for capturing analog images and an electronic screen for displaying the captured analog images as digital images, and an adapter for coupling the mobile device to the endoscope so that the analog image provided by the endoscope is displayed as a digital image on the electronic screen of the mobile device;

Figures 8, 9:
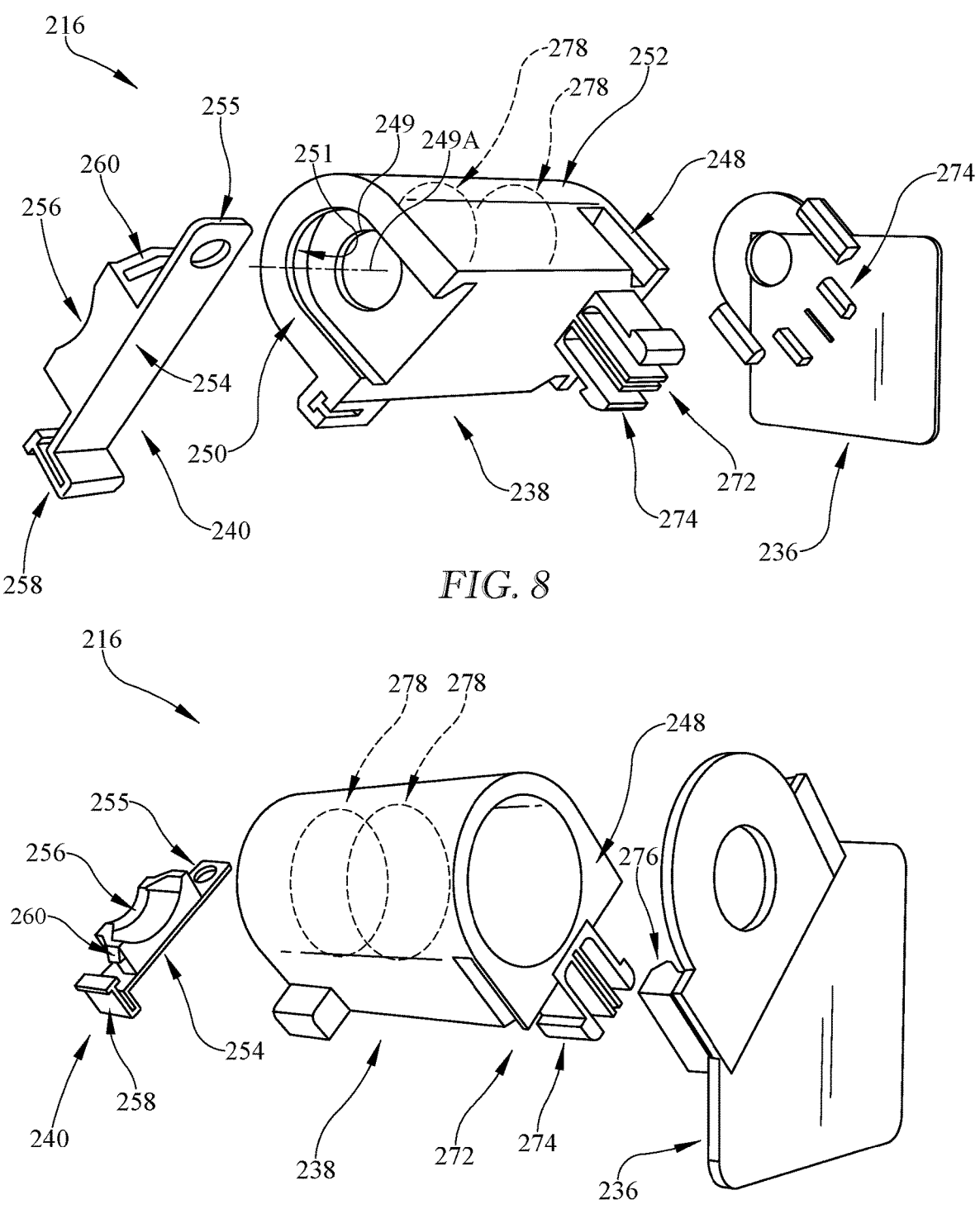
Figures 10, 11:
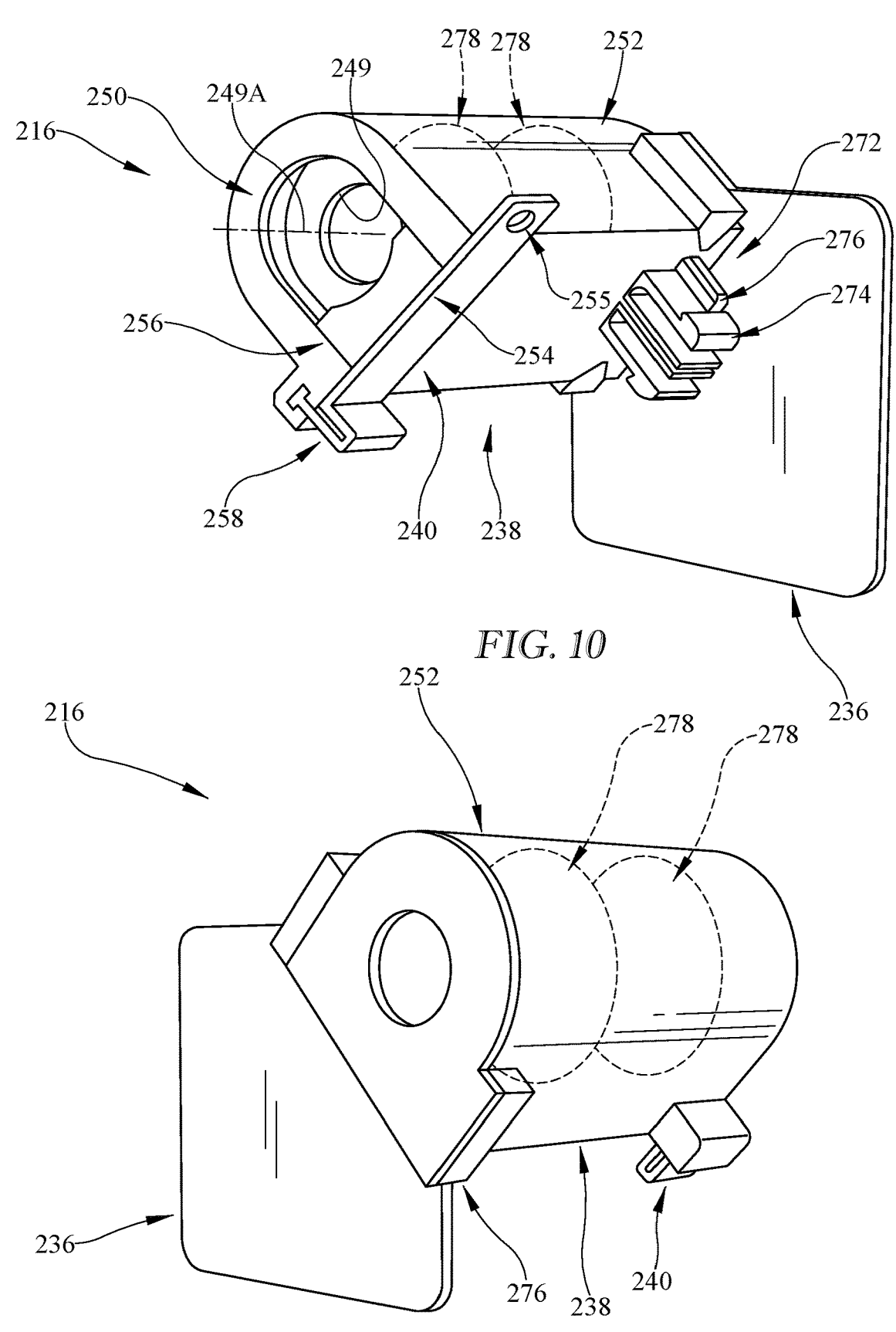
Figures 12, 13:
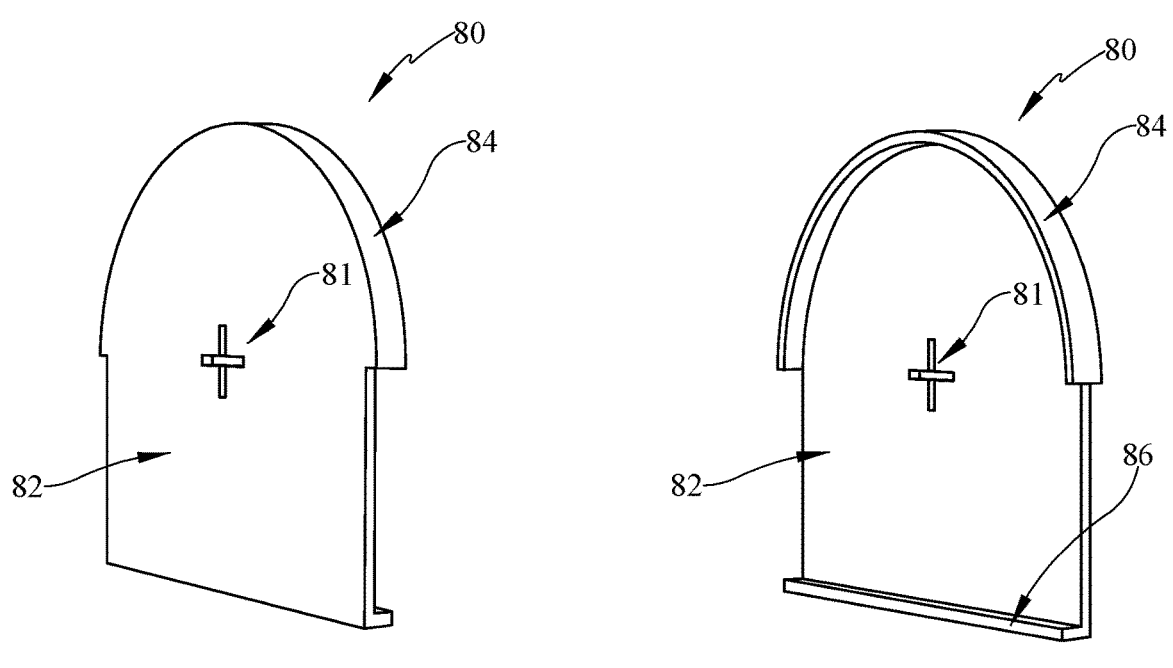
Figure 14:
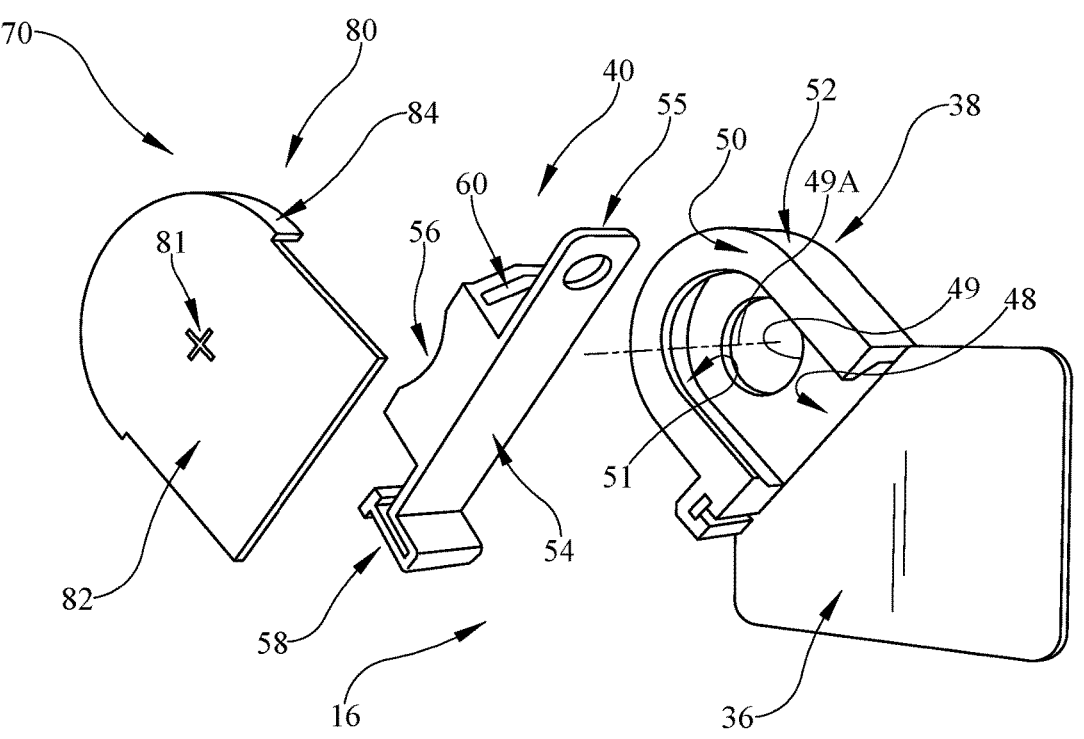
Figures 15, 16:
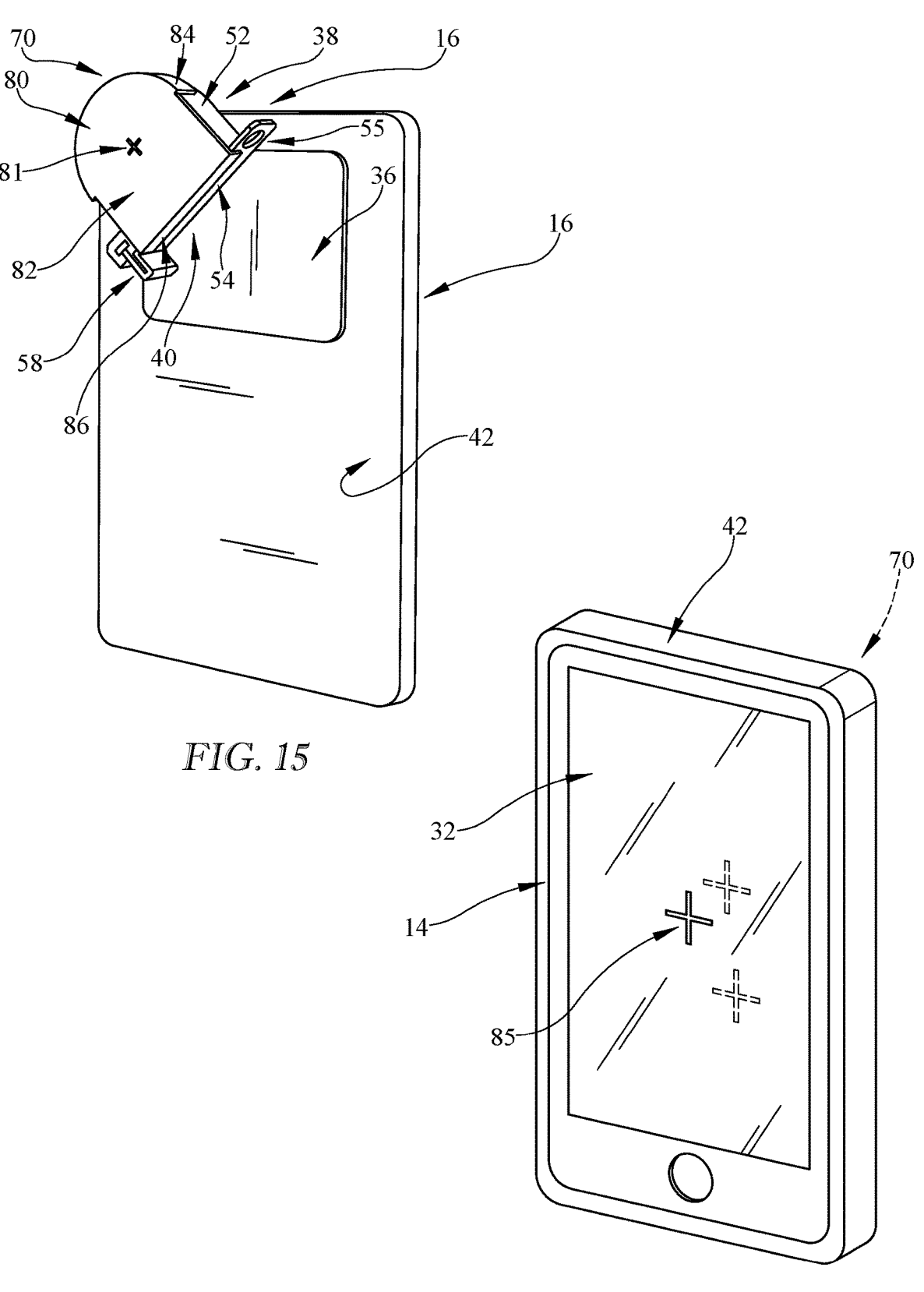

FIG. 8 is an exploded front perspective view of a second adapter according to the present disclosure showing the adapter is made up of the mount pad to be adhered to the mobile device case, a scope receiver configured to be coupled to the mount pad by a releasable clasp, and a scope retainer configured to be coupled to the scope receiver and block removal of an endo scope eyepiece when inserted in the scope receiver as suggested in FIG. 10;

FIG. 9 is an exploded rear perspective view of the adapter from FIG. 8 showing that the scope receiver is formed to include a passageway sized to hold optical lenses for modifying analog images from the endoscope before they are received by the camera of a mobile device;

FIG. 10 is an assembled front perspective view of the adapter from FIGS. 8 and 9 showing that the scope retainer moves into a locked position arranged to block removal of an endoscope eyepiece from the scope receiver when the adapter is assembled;

FIG. 11 is an assembled rear perspective view of the adapter from FIGS. 8-10;

FIG. 12 is a front perspective view of a guide configured to support alignment of the adapter and relative to the mobile device so that the camera port of the scope receiver is located in alignment with the camera lens of the mobile device to ensure a generally centered digital image is displayed on the mobile device;

FIG. 13 is a rear perspective view of the guide from FIG. 12 showing that the guide includes a face plate formed to include a + shape alignment aperture, a cap wall that extends from the face plate to engage a complementary curved surface of the scope receiver, and a foot wall that extends from the face plate to engage a complementary flat surface of the scope retainer;

FIG. 14 is a front exploded assembly view of an adapter kit including the guide along with the mount pad, scope receiver, and scope retainer of the adapter shown in FIGS. 1-7;

FIG. 15 is a front perspective view of the adapter kit fixed to a mobile device and device case at a selected location aligning the adapter to the mobile device so that a generally centered digital image is displayed on the mobile device; and FIG. 16 is a rear perspective view of the adapter kit fixed to a mobile device and device case showing an indicator shape associated with alignment on the electronic screen of the mobile device.

DETAILED DESCRIPTION

Figure 1:

An endoscopy system 10 according to the present disclosure includes an adapter 16 for coupling a mobile device 14 to an endoscope 12 that can be used with most mobile devices as suggested in FIG. 1. A guide 80 can be included that enables proper alignment of the adapter 16 with the mobile device 14 so that a generally centered image is presented on the mobile device 14 from the endoscope 12 as suggested in FIGS. 15 and 16. Further, various embodiments of the adapter 216, 316 can include integrated optical lenses 278, 378 configured to adjust characteristics of images moving from the endoscope 12 to the mobile device 14 through the adapter 16 as suggested in FIGS. 7-11 and 17-18.

Figures 2, 3:
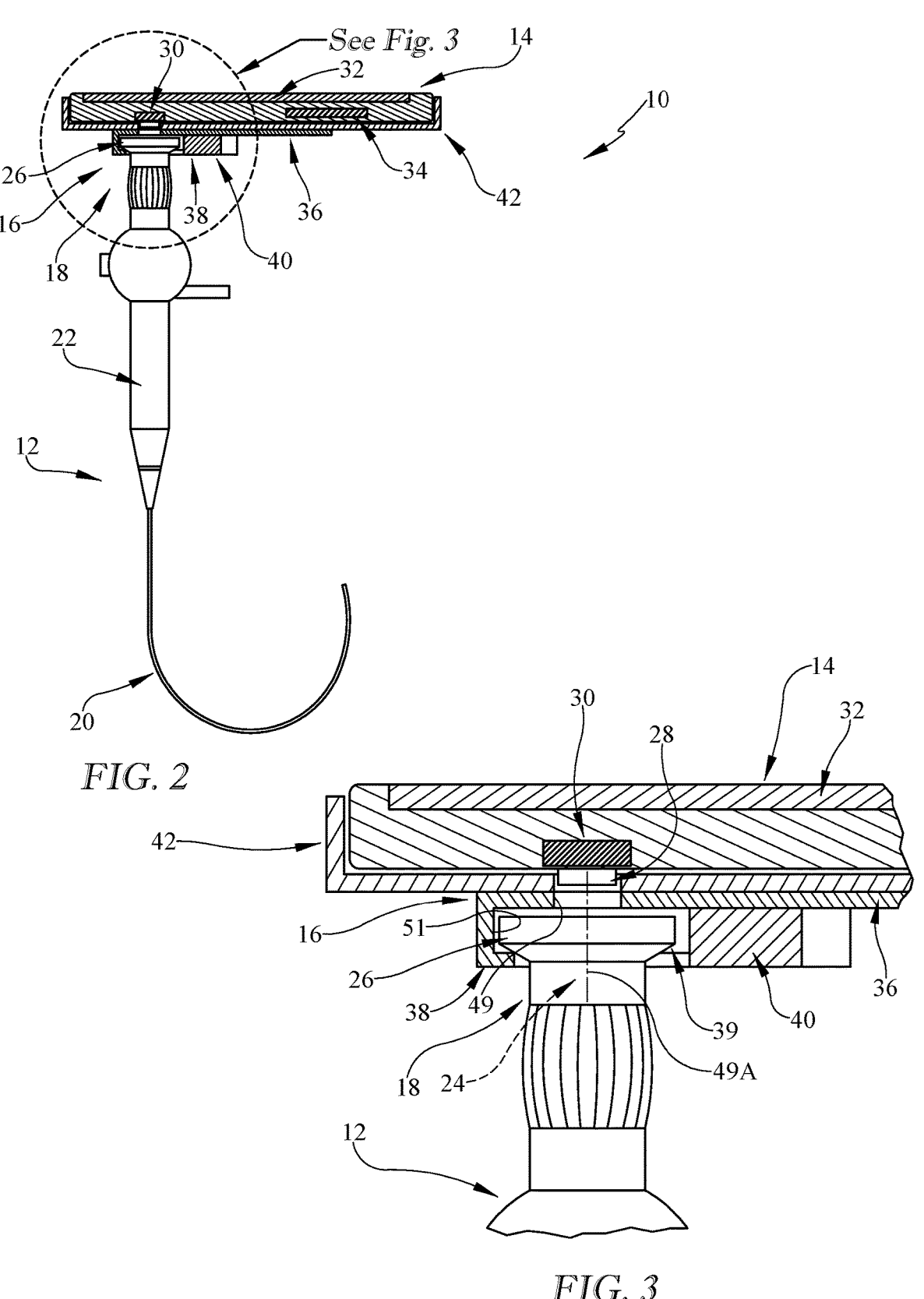
FIG. 2 is a partially cross-sectional view of the endoscopy system of FIG. 1 showing that an eyepiece of the endoscope is captured by the adapter and held in place relative to a camera lens of the mobile device by the adapter.
FIG. 3 is a detail view of a portion of FIG. 2 showing that the adapter includes a mount plate fixed to a mobile device case protecting the mobile device by an adhesive layer.

The endoscopy system 10 shown includes the endoscope 12, the mobile device 14, and the adapter 16 as shown in FIGS. 1-3. The endoscope 12 shown is a flexible design for viewing internal images of a patient to a user. The mobile device 14 is illustratively a cellular phone but could be other various devices such as a tablet computer, webcam, or the like. The adapter 16 is configured to selectively mount the endoscope 12 to the mobile device 14 so that analog images from the endoscope 12 are displayed on the mobile device 14 for viewing and/or recording.

As noted above, the endo scope 12 is a flexible scope configured for insertion into various locations to view remote images as suggested in FIGS. 1 and 2. However, it is contemplated that any suitable endoscope type having an eyepiece can be used with the disclosed adapter 16. For example, features of the disclosed designs can be used with nasal endoscopes for the nasal cavity and sinuses, flexible laryngoscopes for the pharynx and larynx, bronchoscopes for the trachea and bronchi, laparoscopes for the abdomen, and cystoscopes for the bladder, to name a few.

The endoscope 12 includes an eyepiece 18, a flexible fiber optic 20, and a scope body 22 as shown in FIGS. 1 and 2. The eyepiece 18 is made up of a view lens 24 and an eye rest flange 26 shaped to support a user's face around the eye so that images carried to the view lens 24 from the flexible fiber optic 20 can be seen. The flexible fiber optic 20 can be inserted into a patient and carry an image to the view lens 24. The scope body 22 illustratively houses a light source that generates light carried to the free end of the flexible fiber optic 20 and optic lenses that adjust images prior to delivery to the view lens 24.

The mobile device 14 is illustratively provided by a cellular phone as shown in FIGS. 1 and 2. The mobile device 14 includes a camera lens 28 integrated in a camera 30, an electronic screen 32, and a controller 34. The camera lens 28 is arranged on a back side of the mobile device 14 opposite the electronic screen 32 on a front side of the mobile device 14. The controller 34 communicates with both the camera 30 and the screen 32 to display digital images on the screen 32 from the camera 30. Further, the controller 34 has a processor and memory configured to provide for digital magnification of images as well as storage of digital images/videos. As noted above, other mobile devices such as tablet computers, webcams, and other suitable devices can also be used in place of the cellular phone shown.

The adapter 16 supports mounting of the camera lens 28 included in the mobile device 14 as needed relative to the view lens 24 of the endoscope 12 as suggested in FIG. 3. Mounting via the adapter 16 enables analog images from the endoscope 12 to be displayed as digital images on the electronic screen 32 of the mobile device 14. Moreover, the adapter 16 allows for selective removal of the mobile device 14 from the endoscope 12 so that the mobile device can be used for various other functions.

Figures 4, 5, 6, 7:
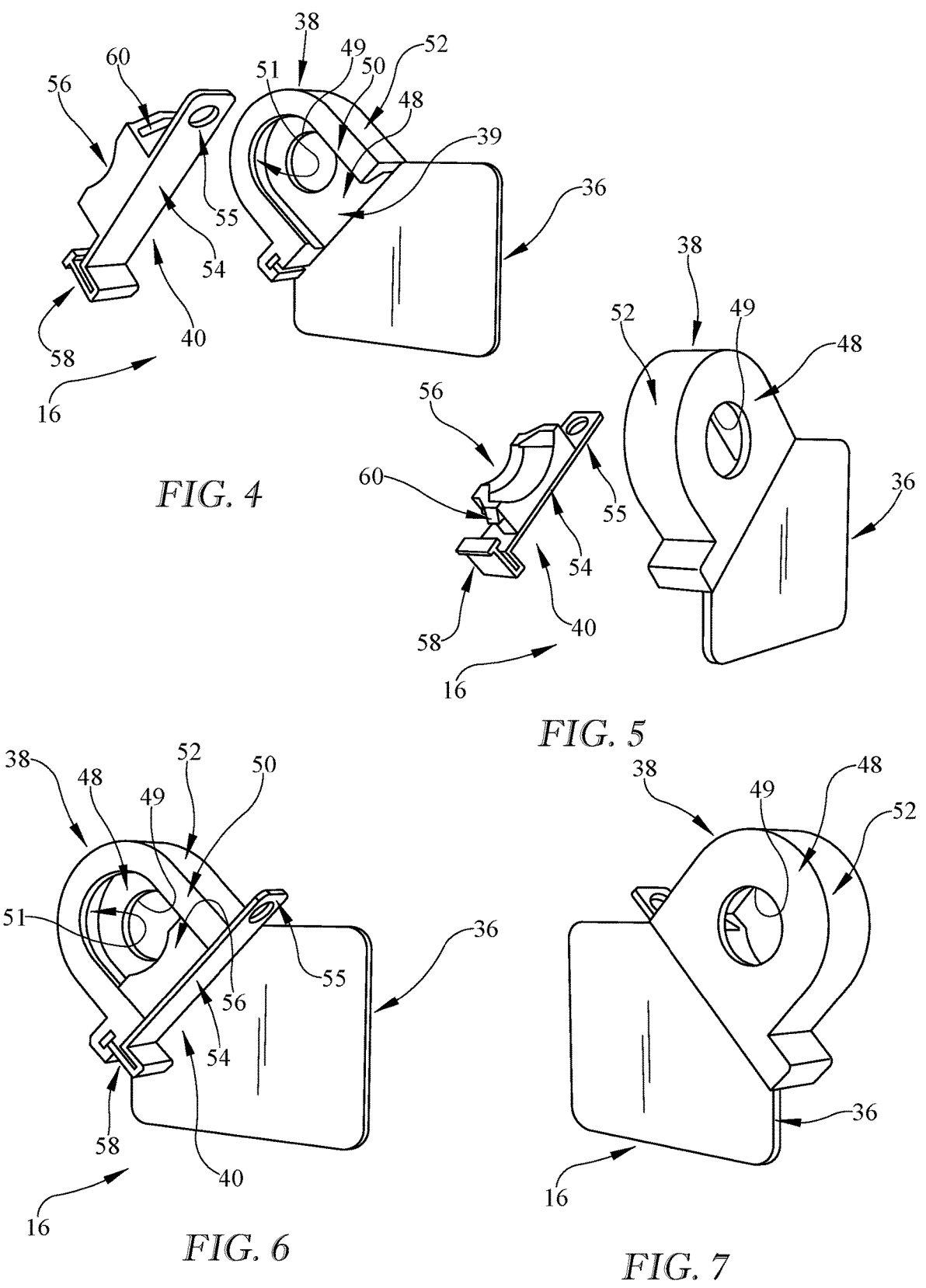
FIG. 4 is an exploded front perspective view of the adapter showing the adapter is made up of the mount pad to be adhered to the mobile device case, a scope receiver integrally coupled to the mount pad, and a scope retainer configured to be coupled to the scope receiver and block removal of an endoscope eyepiece when inserted in the scope receiver as suggested in FIGS. 3 and 6.
FIG. 5 is an exploded rear perspective view of the adapter from FIG. 4 showing that the scope receiver is formed to include a camera port through which the camera lens included in the mobile device can view the endoscope.
FIG. 6 is an assembled front perspective view of the adapter from FIGS. 4 and 5 showing that the scope retainer moves into a locked position arranged to block removal of an endoscope eyepiece from the scope receiver when the adapter is assembled.
FIG. 7 is an assembled rear perspective view of the adapter from FIGS. 4-6 showing that the scope retainer cooperates with the scope receiver to trap an endoscope eyepiece in a pocket of the scope retainer when the adapter is assembled.

The adapter 16 illustratively includes a mount pad 36, a scope receiver 38, a scope retainer 40 as shown in FIGS. 4 and 5. In the illustrative embodiment, the adapter 16 also includes a device case 42 with a camera cutout 45 as shown in FIGS. 1-3. However, it is contemplated that other components of the adapter can be used without the case and/or that the other components of the adapter 16 can be used with an off-the-shelf device case rather than with an adapter-specific model. The mount pad 36 mounts the adapter 16 to the mobile device 14. The scope receiver 38 receives a portion of the endoscope 12 and the scope retainer 40 selectively locks the endoscope 12 in place within the scope receiver 38.

The mount pad 36 of the adapter 16 is illustratively fixed to the device case 42 by an adhesive layer 46 as suggested in FIGS. 1-3. 3. The mount pad 36 is primarily planar in shape with a flat surface facing the device case 42. The mount pad 36 is smaller than a back panel 48 of the device case 42. In the illustrative embodiment, the mount pad 36 has a height less than four inches and width of less than two and one-half inches so as to be smaller than most generally available cell phones and other mobile devices.

The scope receiver 38 of the adapter 16 is integrated with the mount pad 36 of the embodiment shown in FIGS. 1-7. However, in other embodiments, the scope receiver 38 may be removably coupled to the mount pad 36 as suggested in FIGS. 8-10. The scope receiver 38 forms a pocket 39 that receives at least a portion of the eyepiece 18 included in the endoscope 12 to support coupling of the mobile device 14 to the endoscope 12.

The scope receiver 38 of the exemplary embodiment is formed to include a camera-side panel 48 adjacent the mobile device 14, a scope-side panel 50 adjacent to the endoscope 12, and a receiver body panel 52 that extends from the camera-side panel 48 to the scope-side panel 50, spacing the mobile device from the endoscope 12 as suggested in FIG. 3. The camera-side panel 48 has a camera port 49 formed therethrough. The receiver body panel 52 extends away from an edge of the camera-side panel 48 to an edge of the scope-side panel 50 to define a flange-receiver channel 51. The eye rest flange 26 of the endoscope 12 extends into the channel 51.

In the illustrative embodiment, the scope-side panel 50 forms a U-shape when viewed along an axis 49A of the camera port 49 as shown in FIGS. 4 and 6. In this way, the flange-receiver channel 51 has open ends at the gap in the U-shape through which the eye rest flange 26 can pass in a direction perpendicular to the axis 49A when the scope retainer is in the unlocked position.

The scope retainer 40 is movable relative to the scope receiver 38 from a locked position to an unlocked position as suggested in FIGS. 4-7. When the scope retainer 40 is in the locked position, the eye rest flange 26 is blocked from movement out of the pocket 39 of the scope receiver 38 as suggested in FIGS. 6 and 7. When the scope retainer 40 is in the unlocked position, the eye rest flange 26 is allowed to move out of the pocket 39 of the scope receiver 38 as suggested in FIGS. 4 and 5.

The scope retainer 40 is shaped to include a grip flap 54, a plug 56, and a flexible tether 58 as shown in FIG. 4. The grip flap 54 extends across the and beyond the gap formed in the U-shape of the scope-side panel 50 when the scope retainer 40 is in the locked position. The grip flap 54 provides a cantilevered grip tab 55 for pulling the scope retainer 40 away from the locked position as suggested in FIG. 6. The plug 56 extends into the open ends of the flange-receiving channel 51 and the pocket 39 of the scope receiver 38 when the scope retainer 40 is in the locked position. In this way, the plug 56 blocks movement of the eye rest flange 26 out of the scope receiver 38 when the scope retainer 40 is in the locked position. The flexible tether 58 extends from the grip flap 54 and is coupled to the scope receiver 38 to moveably couple the scope retainer 40 to the scope receiver 38. Of course, other couplings or an independent scope retainer are also contemplated.

The scope retainer 40 is further formed to include a flexible rib 60 as shown in FIGS. 4 and 5. The flexible lock rib 60 engages the scope receiver 38 when the scope retainer 40 is in the locked position to resist movement of the scope retainer 40 to the unlocked position.

In some embodiments, the adapter 16 may be provided in an adapter kit 70 with a guide 80 as shown in FIGS. 12-16. The guide 80 is configured to support alignment of the mount pad 36 and scope receiver 38 relative to the mobile device 14. In this way, the camera port 41 of the scope receiver 38 is located in alignment with the camera lens 25 of the mobile device 14 to ensure the generally centered digital image is displayed on the mobile device 14 as suggested in FIG. 16.

The exemplary guide 80 is removably coupled to the scope receiver 38 and is shaped to include an alignment aperture 81 as shown in FIG. 15. The alignment aperture 81 is smaller than the camera port 41 and is arranged along an axis 49A around which the camera port 49 extends. In this way, light passing through the alignment aperture 81 forms an alignment indicator shape 85 displayed on the mobile device 14 as shown in FIG. 16. In the illustrative embodiment, the alignment aperture 81 has a + shape but can have any suitable shape.

The alignment indicator shape 85 can be moved by movement of the mount pad 36 relative to the mobile device 14 and device case 42 to a selected location on the electronic screen 32. The selected location, illustratively the center of the screen, is associated with a generally centered digital image prior to the mount pad 36 and scope receiver 38 being fixed in place relative to the mobile device 14 and device case 42. When the alignment indicator 85 shows in the selected location, the mount pad 36 can be fixed by the adhesive layer to the device case 42 or the mobile device 14 directly. Once the mount pad 36 is fixed, the guide 80 can be removed and retained for future use. In other embodiments, the guide 80 may be provided by a sticker or similar for one time use.

The illustrative guide 80 structurally includes a face plate 82, a cap wall 84, and a foot wall 86 as shown in FIG. 13. The face plate 82 extends over one side of the pocket 39 defined by the scope receiver 38 and is formed to include the alignment aperture 81. The cap wall 84 extends from the face plate 82 to engage a complementary curved surface of the receiver body panel 52 when the guide 80 is coupled to the scope receiver 38. The foot wall 86 that extends from the face plate 82 to engage a complementary flat exterior surface of grip flap 54 when the scope retainer 40 is in the locked position and when the guide 80 is coupled to the scope receiver 38.

A second adapter 216 in accordance with the present disclosure is shown in FIGS. 8-11. The adapter 216 is substantially similar to the adapter 16 shown in FIGS. 1-7 and described herein. Accordingly, similar reference numbers in the 200 series indicate features that are common between the adapter 16 and the adapter 216. The description of the adapter 16 is incorporated by reference to apply to the adapter 216, except in instances when it conflicts with the specific description and the drawings of the adapter 216.

The adapter 216 includes a mount pad 236 that is releasably coupled to the scope receiver 238 by a releasable clasp 272 as shown in FIGS. 8 and 10. The releasable clasp 272 is illustratively provided by a side release male buckle 274 and corresponding catches 276 configured to be engaged by the side release buckle 274. Upon insertion of the buckle 274 into the catches 276, the scope receiver 238 is held in place relative to the mount pad 236.

The adapter 216 includes a scope receiver 238 shaped to house lenses configured to modify images from the endoscope 12 prior to display on the mobile device 14 as suggested in FIG. 10. The scope receiver 238 includes an elongated receiver body panel 252 and a number of lenses 278 coupled to the receiver body panel 252. The lenses 278 are arranged along the axis 249A of the camera port 249 between the associated camera-side panel 248 and the scope-side panel 250. The lenses 278 can adjust brightness, focus, focal length, and magnification of images passing through the adapter 210.

A third adapter 316 in accordance with the present disclosure is shown in FIGS. 17 and 18. The adapter 316 is substantially similar to the adapter 16 shown in FIGS. 1-7 and described herein. Accordingly, similar reference numbers in the 300 series indicate features that are common between the adapter 16 and the adapter 316. The description of the adapter 16 is incorporated by reference to apply to the adapter 316, except in instances when it conflicts with the specific description and the drawings of the adapter 316.

The adapter 316 includes a mount pad 336 that is shaped for use with a webcam providing the mobile device 314. The mount pad 336 extends outwardly from the camera-side panel 348 of the scope receiver 338 so that the overall outline of the mount pad 336 is square.

In addition, the adapter 316 includes a scope receiver 338 shaped to house lenses configured to modify images from the endoscope 12 prior to display on the mobile device 14 as suggested in FIG. 18. The scope receiver 338 includes an elongated receiver body panel 352 and a number of lenses 378 coupled to the receiver body panel 352. The lenses 378 are arranged along the axis 349A of the camera port 349 between the associated camera-side panel 348 and the scope-side panel 30. The lenses 378 are mounted for movement within scope receiver 338 and can adjust brightness, focus, focal length, and magnification of images passing through the adapter 310. Knobs 398 are coupled to lenses 378 and extend out of scope receiver 338 to facilitate movement of the lenses 378 by a user.

The devices disclosed herein adapt endoscopes 12 with mobile devices 14. One version 16 features a port for endoscopic lens pieces that can be mounted onto existing phone cases and aligned to the phone's built-in camera. This version uses the phone's digital magnification to enhance images. A second version 216 includes an endoscopic port, an intervening optical telescope, and can be mounted on existing phone cases and aligned to the phone's built-in camera. A third version 316 utilizes an external optically enhanced camera with a port for an endoscopic lens and a wired connection to laptops or tablets 399.

The invention claimed is:

1. An adapter kit for coupling a mobile device to an endoscope so that a camera lens of the mobile device captures an analog image from the endoscope in order that the analog image is displayed as a digital image on an electronic screen of the mobile device for viewing, the kit comprising
   a mount pad provided by a planar plate adapted to be fixed relative to the mobile device by an adhesive layer when the adapter kit is in place relative to the mobile device so that a generally centered digital image is displayed on the mobile device,
   a scope receiver coupled to the mount pad, the scope receiver shaped to define a pocket sized to receive an eyepiece included in the endoscope and a camera port opening into the pocket through which the camera lens of the mobile device can receive input, and
   a guide configured to support alignment of the mount pad and scope receiver relative to the mobile device so that the camera port of the scope receiver is located in alignment with the camera lens of the mobile device to ensure the generally centered digital image is displayed on the mobile device,
   wherein the guide is removably coupled to the scope receiver and shaped to include an alignment aperture smaller than the camera port that is arranged so that light passing through the alignment aperture forms an alignment indicator shape displayed on the mobile device that can be moved by movement of the mount pad relative to the mobile device to a selected location on the electronic screen, the selected location being associated with the generally centered digital image prior to the mount pad and scope receiver being fixed in place relative to the mobile device.

2. The kit of claim 1, wherein the alignment aperture is arranged along an axis around which the camera port extends.

3. The kit of claim 1, wherein the kit includes a device case shaped to receive the mobile device having a back panel formed to include a camera cutout and the mount pad is smaller than the back panel.

4. The kit of claim 3, wherein the back panel is planar so as to provide a flat surface onto which the mount pad is to be fixed by the adhesive layer.

5. The kit of claim 1, wherein the guide includes a face plate that extends over one side of the pocket defined by the scope receiver and that is formed to include the alignment aperture, and wherein the guide includes a cap wall that extends from the face plate to engage a complementary surface of the scope receiver when the guide is coupled to the scope receiver.

6. The kit of claim 5, further comprising a scope retainer that is movable relative to the scope receiver from a locked position in which the eyepiece is blocked from movement out of the pocket of the scope receiver to an unlocked position in which the eyepiece is allowed to move out of the pocket of the scope receiver.

7. The kit of claim 6, wherein the guide includes a foot wall that extends from the face plate to engage a complementary surface of the scope retainer when the scope retainer is in the locked position and when the guide is coupled to the scope receiver.

8. The kit of claim 1, wherein the alignment aperture has a + shape so that light passing through the alignment aperture forms an alignment indicator with the same shape being displayed on the electronic screen of the mobile device.

9. An endoscopy system, the system comprising
   an endoscope including an eyepiece and an optic, the eyepiece having a view lens and an eye rest flange, and the optic adapted to carry an analog image to the view lens from a location spaced apart from the eyepiece,
   a mobile device including a camera with a camera lens and an electronic screen coupled to the camera, the electronic screen configured to display a digital image based on input from the camera lens,
   a device case that receives the mobile device and has a camera cutout through which the camera lens of the mobile device receives input, and
   an adapter that selectively couples the mobile device and device case to the endoscope so that the camera lens of the mobile device captures the analog image carried to the view lens of the endoscope in order that the analog image is displayed as the digital image on the electronic screen for viewing, wherein the adapter includes a mount pad fixed to the device case by an adhesive layer, a scope receiver coupled to the mount pad and having a pocket that receives the eye rest flange of the eyepiece, and a scope retainer that is movable relative to the scope receiver from a locked position in which the eye rest flange is blocked from movement out of the pocket of the scope receiver to an unlocked position in which the eye rest flange is allowed to move out of the pocket of the scope receive.

10. The system of claim 9, wherein the scope receiver includes a camera-side panel through which the camera port is formed, a receiver body panel that extends away from the camera-side panel, and a scope-side panel that extends from the receiver body panel at a location spaced from the camera-side panel so that a flange-receiver channel into which the eye rest flange extends is formed by the scope receiver.

11. The system of claim 10, wherein the scope receiver further includes at least one lens arranged along an axis of the camera port between the camera side panel and the scope side panel.

12. The system of claim 11, wherein the at least one lens is mounted for movement relative to the scope receiver so as to allow for adjustment of at least one of brightness, focus, focal length, and magnification.

13. The system of claim 10, wherein the scope-side panel forms a U-shape when viewed along an axis of the camera port so that the flange-receiver channel has open ends at the gap in the U-shape through which the eye rest flange can pass in a direction perpendicular to an axis about which the camera port is formed to enter the flange-receiver channel and pocket of the scope receiver when the scope retainer is in the unlocked position.

14. The system of claim 13, wherein the scope retainer includes a plug that extends into the open ends of the flange-receiver channel and the pocket of the scope when the scope retainer is in the locked position to block movement of the eye rest flange out of the scope receiver when the scope retainer is in the locked position.

15. The system of claim 14, wherein the scope retainer includes a flexible lock rib that engages the scope retainer when the scope retainer is in the locked position to resist movement of the scope retainer to the unlocked position.

16. The system of claim 11, wherein the scope retainer is coupled to the mount pad by a releasable clasp.

17. The system of claim 16, wherein the releasable clasp is provided by a side release male buckle and corresponding catches configured to be engaged by the side release buckle to hold the scope retainer in place relative to the mount pad.

18. The system of claim 9, further including a guide configured to support alignment of the mount pad and scope receiver relative to the mobile device so that the camera port of the scope receiver is located in alignment with the camera lens of the mobile device to ensure the generally centered digital image is displayed on the mobile device.

19. The system of claim 18, wherein the guide is removably coupled to the scope receiver and is shaped to include an alignment aperture smaller than the camera port that is arranged so that light passing through the alignment aperture forms an alignment indicator shape displayed on the mobile device.

20. The system of claim 9, wherein the mobile device is selected from one of a cell phone, a tablet computer, and a web camera.

* * * * *